United States Patent [19]

Kaiser et al.

[11] Patent Number: 4,581,172
[45] Date of Patent: Apr. 8, 1986

[54] SUBSTITUTED PYRIMIDO[6,1-A]ISOQUINOLIN-4-ONES,-PYRIMIDO[6,1-A]BENZOZEPIN-4-ONES AND PYRIMIDO[6,1-A]BENZODIAZEPIN-4-ONES USEFUL FOR PREVENTION OF THROMBOSES AND TREATING HYPERTENSION

[75] Inventors: Ado Kaiser, Lausen; Frank Kienzle, Flüh, both of Switzerland

[73] Assignee: Hoffmann-La Roche Inc., Nutley, N.J.

[21] Appl. No.: 603,793

[22] Filed: Apr. 25, 1984

[30] Foreign Application Priority Data

May 5, 1983 [CH] Switzerland .......................... 2442/83
Mar. 20, 1984 [CH] Switzerland .......................... 1392/84

[51] Int. Cl.[4] .................. C07D 471/04; A61K 31/505
[52] U.S. Cl. .................. 260/243.3; 544/246; 544/249; 544/252; 544/316; 544/317; 514/214; 514/267
[58] Field of Search ............... 544/316, 317, 247, 249, 544/252, 246; 260/243.3; 424/251; 514/267, 214

[56] References Cited

U.S. PATENT DOCUMENTS 4,482,556 11/1984 Lal et al. ............................ 424/251

FOREIGN PATENT DOCUMENTS 862785 7/1978 Belgium .
10759 5/1980 European Pat. Off. .
75165 3/1983 European Pat. Off. ............ 544/252
2801289 5/1979 Fed. Rep. of Germany .
46-09466 3/1971 Japan .
46-09467 3/1971 Japan .
1597717 9/1981 United Kingdom .

OTHER PUBLICATIONS

Schölkens et al, Archiv. fur Pharmakologie, vol. 319(Suppl.) R49,196 (1982).
Hoecht Pharm Ltd., Chem. Abst. 94:84152c (1981).
Ruppert et al, Chem. Abst. 97:208034z (1982).
Lal et al, Chem. Abst. 95:73469f (1981).
Capuano et al, Chem. Abst. 43266x (1975).
Lal et al, Chem. Abst. 90:54969z.

Primary Examiner—Donald G. Daus
Assistant Examiner—Cecilia Shen
Attorney, Agent, or Firm—Jon S. Saxe; Bernard S. Leon; William G. Isgro

[57] ABSTRACT

Pyrimidone derivatives of the formula

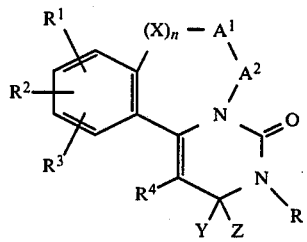

wherein n is the integer 1 or 0; $A^1$ and $A^2$ are independently methylene or mono-lower alkyl or di-lower alkyl methylene; X is methylene, mono-lower alkyl or di-lower alkyl methylene, nitrogen or lower alkyl nitrogen; R is hydrogen or lower alkyl; and Y and Z taken together are the group $=NR^5$, or R and Z taken together form a N—C—bond and Y is a group —N(H)$R^5$; $R^1$, $R^2$ and $R^3$ are hydrogen, lower alkyl or lower alkoxy, or $R^1$ and $R^2$ or $R^2$ and $R^3$ taken together are methylenedioxy or ethylenedioxy; $R^4$ is hydrogen or lower-alkyl; $R^5$ is phenyl or phenyl substituted by one or more of $R^6$, $R^7$ and $R^8$ which, independently, are chlorine, fluorine, bromine, lower-alkyl or lower-alkoxy; and provided that at least one of the methylene groups $A^1$ and $A^2$ is mono-lower alkyl or di-lower alkyl methylene, when $R^4$ is hydrogen and n is 0, and physiologically compatible salts thereof which have blood platelet aggregation-inhibiting activity or have activity on the circulatory system, are described.

The compounds of formula I are obtained starting from corresponding chlorinated or brominated pyrimidone derivatives.

50 Claims, No Drawings

SUBSTITUTED PYRIMIDO[6,1-A]ISOQUINOLIN-4-ONES, PYRIMIDO[6,1-A]BENZOZEPIN-4-ONES AND PYRIMIDO[6,1-A]BENZODIAZEPIN-4-ONES USEFUL FOR PREVENTION OF THROMBOSES AND TREATING HYPERTENSION

BRIEF SUMMARY OF THE INVENTION

The pyrimidone derivatives of the formula

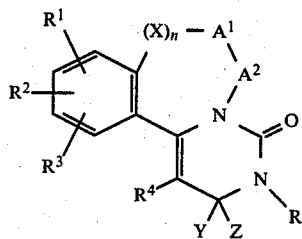

I wherein n is the integer 1 or 0; $A^1$ and $A^2$ are independently methylene or mono-lower alkyl or di-lower alkyl methylene; X is methylene, mono-lower alkyl or di-lower alkyl methylene, nitrogen or lower alkyl nitrogen; R is hydrogen or lower-alkyl; Y and Z taken together are the group $=NR^5$, or R and Z taken together form a N—C-bond and Y is —N(H)$R^5$; $R^1$, $R^2$ and $R^3$ are hydrogen, lower-alkyl or lower-alkoxy, or $R^1$ and $R^2$ or $R^2$ and $R^3$ taken together are methylenedioxy or ethylenedioxy; $R^4$ is hydrogen or lower-alkyl; $R^5$ is phenyl or phenyl substituted by one or more of $R^6$, $R^7$ and $R^8$ which, independently, are chlorine, fluorine, bromine, lower-alkyl or lower-alkoxy; and provided that at least one of $A^1$ and $A^2$ is mono-lower alkyl or di-lower alkyl methylene when $R^4$ is hydrogen and n is 0,
and physiologically compatible salts thereof, are described. The compounds of formula I are useful as agents for the prevention of thromboses and as antihypertensive agents.

DETAILED DESCRIPTION OF THE INVENTION

The invention relates to pyrimidone derivatives of formula I set forth hereinafter, a process for their preparation and pharmaceutical compositions based on the compounds of formula I.

The pyrimidone derivatives of the invention are characterized by the formula

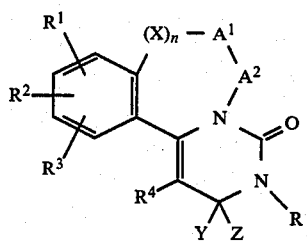

I wherein n is the integer 1 or 0; $A^1$ and $A^2$ are independently methylene or mono-lower alkyl or di-lower alkyl substituted methylene; X is methylene, mono-lower alkyl or di-lower alkyl substituted methylene, nitrogen or lower alkyl nitrogen; R is hydrogen or lower-alkyl; Y and Z taken together are the group $=NR^5$, or R and Z taken together form a N—C-bond and Y is (H)$R^5$; $R^1$, $R^2$ and $R^3$ are hydrogen, lower-alkyl or lower-alkoxy, or $R^1$ and $R^2$ or $R^2$ and $R^3$ taken together are methylenedioxy or ethylenedioxy; $R^4$ is hydrogen or lower-alkyl; $R^5$ is phenyl or phenyl substituted by one or more of $R^6$, $R^7$ and $R^8$ which, independently, are chlorine, fluorine, bromine, lower-alkyl or lower-alkoxy; and provided that at least one of $A^1$ and $A^2$ is mono-lower alkyl or di-lower alkyl substituted methylene when $R^4$ is hydrogen and n is 0,
and physiologically compatible salts thereof.

As used herein, the term "lower" denotes straight-chain or branched-chain groups containing 1-6, preferably 1-4, carbon atoms, for example, methyl, ethyl, propyl, isopropyl, n-butyl and isobutyl, as well as alkoxy groups corresponding to these alkyl groups. Chlorine is preferred.

The pyrimidone derivatives of formula I of the invention can contain one or more asymmetric carbon atoms and can therefore exist as optically active enantiomers, diastereomers or racemates. Further, the pyrimidone derivatives of formula I of the invention, especially those compounds of formula I and salts thereof wherein R is hydrogen and Y and Z taken together are the group $=NR^5$ or wherein R and Z taken together form a N—C-bond and Y is —(H)$R^5$, can exist in various tautomeric forms. The foregoing enantiomers, diastereomers, racemates and tautomers also form part of the invention.

The compounds of formula I form salts with acids and these salts also form part of the invention. Examplary of such salts are salts with physiologically compatible or pharmaceutically acceptable mineral acids, such as, hydrochloric acid, hydrobromic acid, sulfuric acid, phosphoric acid or the like; or with organic acids such as methanesulfonic acid, acetic acid, propionic acid, citric acid, succinic acid, malic acid, fumaric acid, phenylacetic acid, salicylic acid or the like.

Preferred pyrimidone derivatives of formula I are those in which $R^1$ is hydrogen and $R^2$ and $R^3$ are lower-alkoxy, especially methoxy, in the para-position to the angular carbon atoms of the phenyl ring; X, $A^1$ and $A^2$ are optionally monomethylated or dimethylated methylene, or X is optionally methylated nitrogen; or one or more of $R^6$, $R^7$ and $R^8$ are, independently, chlorine, bromine, lower-alkyl or lower-alkoxy.

Still more preferred are the compounds of formula I wherein n is 0 or 1, X is methylene, one of $A^1$ and $A^2$ is methylene and the other is monomethylated methylene, especially the compounds in which the carbon atom of a monomethylated methylene group $A^1$ has the R-configuration or the carbon atom of a monomethylated methylene group $A^2$ has the S-configuration, and further those compounds in which R is hydrogen or methyl or R and Z taken together form a N—C-bond, as well as those in which $R^4$ is hydrogen or $R^5$ is mesityl or 2,6-xylyl.

Further preferred pyrimidone derivatives of formula I are those in which $R^1$ is hydrogen and $R^2$ and $R^3$ are lower-alkoxy, especially methoxy, in the paraposition to the angular carbon atoms of the phenyl ring, n is the number 0 or 1, X is methylene, one of $A^1$ and $A^2$ is methylene and the other is monomethylated methylene, the carbon atom of a monomethylated methylene group $A^1$ having the R-configuration or the carbon atoms of a monomethylated methylene group $A^2$ having the S-configuration, R is hydrogen or methyl or R and Z together form a N—C-bond, $R^4$ is hydrogen and $R^5$ is mesityl or 2,6-xylyl.

Exemplary of the most preferred compounds of formula I are:

(S)-9,10-Dimethoxy-3,6-dimethyl-2-mesitylimino-2,3,6,7-tetrahydro-4H-pyrimido[6,1-a]isoquinolin-4-one, (S)-6-ethyl-6,7-dihydro-9,10-dimethoxy-2-mesitylamino-4H-pyrimido[6,1-a]isoquinolin-4-one, (S)-6-ethyl-9,10-dimethoxy-2-mesitylimino-3-methyl-2,3,6,7-tetrahydro-4H-pyrimido[6,1-a]isoquinolin-4-one, (S)-6-ethyl-6,7-dihydro-9,10-dimethoxy-2-(2,6-xylidino)-4H-pyrimido[6,1-a]isoquinolin-4-one, (S)-6-ethyl-9,10-dimethoxy-3-methyl-2,3,6,7-tetrahydro-2-(2,6-xylylimino)-4H-pyrimido[6,1-a]isoquinolin-4-one, 6,7-dihydro-9,10-dimethoxy-2-mesitylamino-6-methyl-4H-pyrimido[6,1-a]isoquinolin-4-one;

9,10-dimethoxy-3,6-dimethyl-2-mesitylimino-2,3,6,7-tetrahydro-4H-pyrimido[6,1-a]isoquinolin-4-one;

10,11-dimethoxy-2-mesitylimino-3-methyl-2,3,7,8-tetrahydro-4H-6H-pyrimido[6,1-a]benzazepin-4-one;

(S)-6,7-dihydro-9,10-dimethoxy-2-mesitylamino-6-methyl-4H-pyrimido[6,1-a]isoquinolin-4-one;

(S)-6,7-dihydro-9,10-dimethoxy-6-methyl-2-(2,6-xylidino)-4H-pyrimido[6,1-a]isoquinolin-4-one;

(S)-9,10-dimethoxy-3,6-dimethyl-2,3,6,7-tetrahydro-2-(2,6-xylylimino)-4H-pyrimido[6,1-a]isoquinolin-4-one; and (R)-9,10-dimethoxy-3,7-dimethyl-2-mesitylimino-2,3,6,7-tetrahydro-4H-pyrimido[6,1-a]isoquinolin-4-one.

The compounds of formula I of the invention can be prepared by (a) reacting a compound of the formula

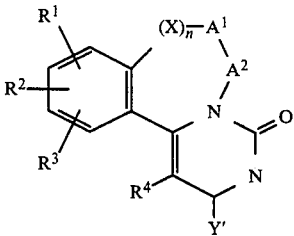

II wherein Y' is chlorine or bromine and the remaining symbols are as previously described,
with an amine of the formula $R^5NH_2$, wherein $R^5$ is as previously described, (b) if desired, reacting a compound of formula I in which R is hydrogen and Y and Z taken together are a group $=NR^5$ or in which R and Z taken together form a N—C-bond and Y is a group —N(H)$R^5$, and $R^5$ has the significance given above, with a lower-alkyl halide, (c) isolating the product of step (a) or (b) in the form of a free base of formula I or a physiologically compatible salt thereof.

Process step (a) can be carried out in a solvent, preferably an aprotic solvent, for example, a halogenated hydrocarbon such as chloroform, conveniently in the presence of a base, for example, a tri-(lower-alkyl)amine, such as triethylamine, or an alkali metal carbonate, such as, sodium carbonate or potassium carbonate, at a temperature up to the reflux temperature of the reaction mixture. There are thus obtained compounds of formula I in which R is hydrogen and Y and Z together are a group $=NR^5$ or in which R and Z taken together are a N—C-bond and Y is a group —N(H)$R^5$, and $R^5$ is as previously described.

Process step (b) can be carried out in a polar solvent, for example, a ketone, such as acetone or an amide, such as dimethylformamide, at a temperature up to the reflux temperature of the reaction mixture, preferably at about 100° C. The reaction is conveniently carried out in the presence of a base, for example, an alkali metal carbonate or a hindered tertiary amine, for example, a tri(lower-alkyl)amine, such as, triethylamine. There are thus obtained compounds of formula I in which R is lower-alkyl and Y and Z taken together are a group $=NR^5$ wherein $R^5$ is as previously described.

The pyrimidone starting materials of formula II can be prepared by reacting a compound of the formula

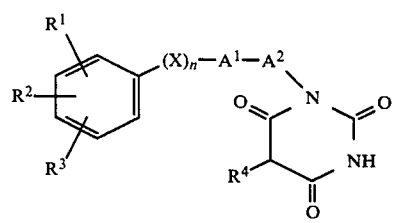

III wherein n, X, $A^1$, $A^2$ and $R^1$-$R^4$ are as previously described,
with an inorganic acid chloride or acid bromide or with the corresponding inorganic chloride or bromide.

This reaction can be carried out using an inorganic acid chloride or acid bromide, for example, phosphorus oxychloride, phosphorus oxybromide or thionyl chloride, at a temperature up to the reflux temperature of the reaction mixture or using an inorganic chloride or bromide corresponding to the acid chloride or acid bromide, for example, phosphorus pentachloride, at a temperature up to about 100° C.

The barbituric acid derivatives of formula III can be prepared starting from the corresponding amines of the formula

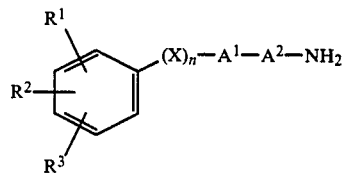

IV wherein n, X, $A^1$, $A^2$ and $R^1$-$R^3$ have the significance given above,
via urea derivatives of the formula

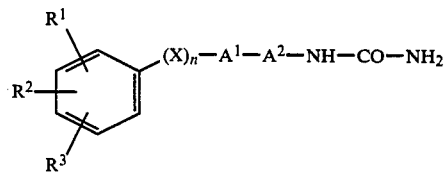

V wherein n, X, $A^1$, $A^2$ and $R^1$-$R^3$ are as previously described,

Conveniently, an amine of formula IV is reacted with an alkali isocyanate, for example, sodium isocyanate, in the presence of an inorganic acid, for example, hydrochloric acid in an aqueous protic solvent, for example, an alcohol, such as, ethanol. The urea derivative of formula V obtained can then be reacted with a malonic acid derivative of the formula $R^4CH(COOR^6)_2$, wherein $R^4$ is as previously described and $R^6$ is lower-alkyl, for example diethyl malonate, in an alcohol such as methanol or ethanol in the presence of an alkali metal alcoholate, for example, sodium methanolate or sodium ethanolate.

The amines of formula IV are known compounds or can be prepared in a known manner; for example, as described in J. Med. Chem. 16, 1973, 480 or in Tetrahedron 31, 1975, 2595.

The pyrimidone derivatives of formula I of the invention can be used as medicaments. They inhibit the aggregation of blood platelets and can therefore be used for the prevention of thromboses. Moreover, they have activity on the circu-atory system, especially antihypertensive activity, and can be used for the treatment or prevention of cardiovascular illnesses.

The pyrimidone derivatives of formula I of the invention can be used as medicaments, for example in the form of pharmaceutical preparations which contain them or their salts in admixture with a pharmaceutical, organic or inorganic inert carrier material which is suitable for enteral, percutaneous or parenteral administration, for example, water, gelatine, gum arabic, lactose, starch, magnesium stearate, talc, vegetable oils, polyalkylene glycols or Vaseline. The pharmaceutical preparations can be made up in solid form, for example, as tablets, dragées, suppositories or capsules, in semi-solid form, for example, as ointments or in liquid form, for example, as solutions, suspensions or emulsions. The pharmaceutical preparations may be sterilized and/or may contain adjuvants such as preserving, stabilizing, wetting or emulsifying agents, salts for varying the osmotic pressure or buffers. They can also contain still other therapeutically valuable substances.

The pyrimidone derivatives of formula I of the invention are preferably administered orally. For adults, there come into consideration an oral daily dosage of 0.1 to 30 mg/kg and a parenteral daily dosage of 0.01 to 10 mg/kg, in each case having regard to the individual requirements of the patient and the dosage form.

The aggregation-inhibiting activity was demonstrated according to the aggregometer method (Nature 194, 1962, 927; 231, 1971, 220). The maximum aggregation velocity was taken as the test parameter and the effective concentration ($EC_{50}$) was ascertained from dosage-activity curves. Human platelet-rich plasma was obtained by centrifugation from citrated venous blood. The experiments were carried out with suspensions of the test substances in 0.9% sodium chloride. 0.18 ml of citrate plasma was treated with a 10 μl suspension of the test compounds and the mixture was incubated at 37° C. for 10 minutes, whereupon the aggregation was initiated by the addition of 10 μl of a suspension of collagen fibrils. The following $EC_{50}$ values (in μM) were ascertained for the hydrochlorides of the products of certain Examples hereinafter:

| Example | 2(a) | 3 | 4(a) | 5(a) |
|---|---|---|---|---|
| $EC_{50}$ | 0.11 | 0.6 | 0.10 | 0.12 |

9,10-Dimethoxy-3,7-dimethyl-2-(o-tolylimino)-2,3,6,7-tetrahydro-4H-pyrimido[6,1-a]isoquinolin-4-one hydrochloride [the product of Example 6a) 2.] demonstrated an $LD_{50}$ of 2500 mg/kg p.o. in mice.

The Examples which follow further illustrate the invention. All temperatures are in degrees Centigrade unless otherwise stated.

EXAMPLE 1

A. Preparation of 6,7-dihydro-9,10-dimethoxy-2-mesitylamino-7-methyl-4H-pyrimido[6,1-a]isoquinolin-4-one (a) 0.3 mol of 3,4-dimethoxy-β-methylphenethylamine is dissolved in 300 ml of ethanol and the solution is treated with 0.3 mol of 1N hydrochloric acid. At 50° C. there is then added portionwise thereto a total of 0.31 mol of sodium isocyanate in the course of 90 minutes. The urea derivative corresponding to the amine starting material crystallizes out upon cooling. Pure (3,4-dimethoxy-β-methylphenethyl)urea is removed by filtration and washed with cold water. M.p. 179°–180° C.

(b) 7.25 g of sodium are dissolved in 420 ml of ethanol. To this solution is added 0.315 mol of diethyl malonate, followed by 0.3 mol of (3,4-dimethoxy-β-methylphenethyl)-urea (dissolved in 250 ml of ethanol). The mixture is boiled under reflux for 20 hours, then cooled and treated with 500 ml of 1N hydrochloric acid. The precipitated 1-(3,4-dimethoxy-β-methylphenethyl)barbituric acid is removed by filtration and washed with aqueous ethanol. M.p. 85°–96° C.

(c) 0.1 mol of 1-(3,4-dimethoxy-β-methylphenethyl)barbituric acid is dissolved in 300 ml of phosphorus oxychloride and the solution is boiled under reflux for 18 hours. The solution is evaporated and the residue is taken up in a mixture of ice, water and chloroform and adjusted to pH 9 with 28% sodium hydroxide solution. The organic phase is separated; it contains 2-chloro-6,7-dihydro-9,10-dimethoxy-7-methyl-4H-pyrimidino[6,1-a]isoquinolin-4-one.

A small portion of this organic phase is evaporated. The residue is dissolved in ethyl acetate and the solution is chromatographed on silica gel. After recrystallization from ethyl acetate/hexane, there is obtained the pure product, m.p. 219°–220° C.

B. Preparation of the end-product 100 ml of 2,4,6-trimethylaniline are added to the largest part of the organic phase obtained in step A.(c) and the mixture is boiled under reflux for 20 hours. The solution is then evaporated and the residue is dissolved in ethyl acetate and chromatographed on silica gel. Pure 6,7-dihydro-9,10-dimethoxy-2-mesitylamino-7-methyl-4H-pyrimido[6,1-a]isoquinolin-4-one is isolated as the hydrochloride, m.p. 191°–193° C., (80% yield), after treatment with hydrochloric acid.

EXAMPLE 2

In a manner analogous to that described in Example 1, (a) starting from 3,4-dimethoxy-α-methylphenethylamine via (3,4-dimethoxy-α-methylphenethyl)urea, m.p. 172° C., and (3,4-dimethoxy-α-methylphenethyl)barbituric acid, m.p. 162°–164° C.

there was prepared 6,7-dihydro-9,10-dimethoxy-2-mesitylamino-6-methyl-4H-pyrimido[6,1-a]isoquinolin-4-one;

m.p. of the hydrochloride is 199° C.

(b) starting from 3,4-dimethoxy-β-β-dimethylphenethylamine via (3,4-dimethoxy-β,β-dimethylphenethyl)urea, m.p. 152° C., and (3,4-dimethoxy-β,β-dimethylphenethyl)barbituric acid, m.p. 172° C., there was prepared 6,7-dihydro-9,10-dimethoxy-2-mesitylamino-7,7-dimethyl-4H-pyrimido[6,1-a]isoquinolin-4-one; m.p. of the hydrochloride is 203°–205° C.

EXAMPLE 3

Preparation of 9,10-dimethoxy-3,7-dimethyl-2-mesitylimino-2,3,6,7-tetrahydro-4H-pyrimido[6,1-a]isoquinolin-4-one 18 g of 6,7-dihydro-9,10-dimethoxy-2-mesitylamino-7-methyl-4H-pyrimido[6,1-a]isoquinolin-4-one are boiled under reflux in 1.5 l of acetone with 270 ml of methyl iodide in the presence of 90 g of potassium carbonate. The mixture is then filtered and the filtrate is evaporated. The residue is dissolved in chloroform and purified by chromatography on a silica gel column. There are obtained 9.4 g of pure 9,10-dimethoxy-3,7-dimethyl-2-mesitylimino-2,3,6,7-tetrahydro-4H-pyrimido[6,1-a]isoquinolin-4-one, m.p. 156°–157° C. The corresponding hydrochloride of the compound melts at 224° C. (decomposition).

EXAMPLE 4

In a manner analogous to that described in Example 3, (a) starting from 6,7-dihydro-9,10-dimethoxy-2-mesitylamino-6-methyl-4H-pyrimido[6,1-a]isoquinolin-4-one there was prepared 9,10-dimethoxy-3,6-dimethyl-2-mesitylimino-2,3,6,7-tetrahydro-4H-pyrimido[6,1-a]isoquinolin-4-one, m.p. of the hydrochloride is 224° C.;

(b) starting from 6,7-dihydro-9,10-dimethoxy-7,7-dimethyl-2-mesitylamino-4H-pyrimido[6,1-a]isoquinolin-4-one there was prepared 9,10-dimethoxy-2-mesitylimino-2,3,6,7-tetrahydro-3,7,7-trimethyl-4H-pyrimido[6,1-a]isoquinolin-4-one, m.p. of the hydrochloride is 192°–194° C.

EXAMPLE 5

In a manner analogous to that described in Examples 1 and 3, (a) starting from 3-(3,4-dimethoxyphenyl)propylamine via [3-(3,4-dimethoxyphenyl)propyl]urea, m.p. 165°–166° C., and 1-[3-(3,4-dimethoxyphenyl)propyl]barbituric acid, m.p. 119°–121° C., there was prepared 10,11-dimethoxy-2-mesitylimino-3-methyl-2,3,7,8-tetrahydro-4H,6H-pyrimido[6,1-a]benzazepin-4-one, m.p. of the hydrochloride is 212°–214° C.

(b) starting from 3,4-dimethoxyphenethylamine via 3,4-dimethoxyphenethylurea and 1-(3,4-dimethoxyphenethyl)-5-methylbarbituric acid, m.p. 164°–165° C., there was prepared 9,10-dimethoxy-1,3-dimethyl-2-mesitylimino-2,3,6,7-tetrahydro-4H-pyrimido[6,1-a]isoquinolin-4-one, m.p. of the hydrochloride is 160° C.;

(c) starting from 4-methoxy-β,β-dimethylphenethylamine via (4-methoxy-β,β-dimethylphenthyl)urea, m.p. 137° C., and (4-methoxy-β,β-dimethylphenethyl)barbituric acid, m.p. 175° C., there was prepared 2-mesitylimino-10-methoxy-2,3,6,7-tetrahydro-3,7,7-trimethyl-4H-pyrimido[6,1-a]isoquinolin-4-one, m.p. of the hydrochloride is 216°–217° C.

EXAMPLE 6

The following compounds were prepared in a manner analogous to Examples 1 and 3:

(a) 1. 6,7-Dihydro-9,10-dimethoxy-7-methyl-2-(o-toluidino)-4H-pyrimido[6,1-a]isoquinolin-4-one and
2. 9.10-dimethoxy-3,7-dimethyl-2-(o-tolylimino)-2,3,6,7-tetrahydro-4H-pyrimido[6,1-a]isoquinolin-4-one, m.p. of the hydrochloride is 192°–193° C.;

(b) 1. 6,7-dihydro-9,10-dimethoxy-7-methyl-2-(2,6-xylidino)-4H-pyrimido[6,1-a]isoquinolin-4-one and
2. 9,10-dimethoxy-3,7-dimethyl-2,3,6,7-tetrahydro-(2,6-xylylimino)-4H-pyrimido[6,1-a]isoquinolin-4-one, m.p. of the hydrochloride is 241°–242° C.;

(c) 1. 6,7-dihydro-9,10-dimethoxy-2-(3,5-dimethoxyanilino)-7-methyl-4H-pyrimido[6,1-a]isoquinolin-4-one and
2. 2,3,6,7-tetrahydro-9,10-dimethoxy-3,7-dimethyl-2-(3,5-dimethoxyphenylimino)-4H-pyrimido[6,1-a]isoquinolin-4-one, m.p. of the hydrochloride is 226° C.;

(d) 1. 6,7-dihydro-9,10-dimethoxy-7-methyl-2-(3,4,5-trimethoxyanilino)-4H-pyrimido[6,1-a]isoquinolin-4-one and
2. 9,10-dimethoxy-3,7-dimethyl-2,3,6,7-tetrahydro-2-(3,4,5-trimethoxyphenylimino)-4H-pyrimido[6,1-a]isoquinolin-4-one, m.p. of the hydrochloride is 256°–257° C.;

(e) 1. 6,7-dihydro-9,10-dimethoxy-2-(p-fluoroanilino)-7-methyl-4H-pyrimido[6,1-a]isoquinolin-4-one and
2. 2,3,6,7-tetrahydro-9,10-dimethoxy-3,7-dimethyl-2-(p-fluorophenylimino)-4H-pyrimido[6,1-a]isoquinolin-4-one,
m.p. of the hydrochloride is 240° C.;

(f) 1. 6,7-dihydro-9,10-dimethoxy-7-methyl-2-(2,4-xylidino)-4H-pyrimido[6,1-a]isoquinolin-4-one and
2. 9.10-dimethoxy-3,7-dimethyl-2,3,6,7-tetrahydro-2-(2,4-xylylimino)-4H-pyrimido[6,1-a]isoquinolin-4-one, m.p. of the hydrochloride is 230°–231° C.;

(g) 1. 2-anilino-6,7-dihydro-9,10-dimethoxy-7-methyl-4H-pyrimido[6,1-a]isoquinolin-4-one and 2. 9,10-dimethoxy-3,7-dimethyl-2-phenylimino-2,3,6,7-tetrahydro-4H-pyrimido[6,1-a]isoquinolin-4-one, m.p. of the hydrochloride is 232°–233° C.;
(h) 1. 6,7-dihydro-9,10-dimethoxy-2-(p-methoxyanilino)-7-methyl-4H-pyrimido[6,1-a]isoquinolin-4-one and
2. 9,10-dimethoxy-3,7-dimethyl-2-(p-methoxyphenylimino)-2,3,6,7-tetrahydro-4H-pyrimido[6,1-a]isoquinolin-4-one, m.p. of the hydrochloride is 215° C.;
(i) 1. 6,7-dihydro-9,10-dimethoxy-2-(m-fluoroanilino)-7-methyl-4H-pyrimido[6,1-a]isoquinolin-4-one and
2. 9,10-dimethoxy-3,7-dimethyl-2-(m-fluorophenylimino)-2,3,6,7-tetrahydro-4H-pyrimido[6,1-a]isoquinolin-4-one, m.p. of the hydrochloride is 228°–230° C.;
(j) 1. 2-(6-chloro-2-toluidino)-6,7-dihydro-9,10-dimethoxy-7-methyl-4H-pyrimido[6,1-a]isoquinolin-4-one and
2. 2-(6-chloro-2-tolylimino)-9,10-dimethoxy-3,7-dimethyl-2,3,6,7-tetrahydro-4H-pyrimido[6,1-a]isoquinolin-4-one,
m.p. of the hydrochloride is 211°–212° C.;
(k)1. 2-(2,6-diethylanilino)-6,7-dihydro-9,10-dimethoxy-7-methyl-4H-pyrimido[6,1-a]isoquinolin-4-one and
2. 2-(2,6-diethylphenylimino)-9,10-dimethoxy-3,7-dimethyl-2,3,6,7-tetrahydro-4H-pyrimido[6,1-a]isoquinolin-4-one, m.p. of the hydrochloride is 196°–197° C.;
(l)1. 6,7-dihydro-2-(2,6-diisopropylanilino)-9,10-dimethoxy-7-methyl-4H-pyrimido[6,1-a]isoquinolin-4-one and
2. 2-(2,6-diisopropylphenylimino)-9,10-dimethoxy-3,7-dimethyl-2,3,6,7-tetrahydro-4H-pyrimido[6,1-a]isoquinolin-4-one, m.p. of the hydrochloride is 233° C.

EXAMPLE 7

The following compounds were prepared in a manner analogous to Examples 1 and 3:
(a) starting from α-ethyl-3,4-dimethoxyphenethylamine,
m.p. of the hydrochloride is 150°–152° C.;
1. 6-ethyl-6,7-dihydro-9,10-dimethoxy-2-mesitylamino-4H-pyrimido[6,1-a]isoquinolin-4-one, m.p. of the hydrochloride is 219° C., and
2. 6-ethyl-9,10-dimethoxy-2-mesitylimino-3-methyl-2,3,6,7-tetrahydro-4H-pyrimido[6,1-a]isoquinolin-4-one, m.p. of the hydrochloride is 207°–209° C.;
(b) starting from 2-amino-3-(3,4-dimethoxyphenyl)butane,
1. 6,7-dihydro-9,10-dimethoxy-6,7-dimethyl-2-mesitylamino-4H-pyrimido[6,1-a]isoquinolin-4-one and
2. 9,10-dimethoxy-2-mesitylimino-2,3,6,7-tetrahydro-3,6,7-trimethyl-4H-pyrimido[6,1-a]isoquinolin-4-one, m.p. of the hydrochloride is 236°–237° C.;
(c) starting from 3,4-diethoxy-α-methylphenethylamine,
m.p. of the hydrochloride is 144°–146° C.;
1. 9,10-diethoxy-6,7-dihydro-2-mesitylamino-6-methyl-4H-pyrimido[6,1-a]isoquinolin-4-one, m.p. of the hydrochloride 208°–210° C., and
2. 9,10-diethoxy-3,6-dimethyl-2-mesitylimino-2,3,6,7-tetrahydro-4H-pyrimido[6,1-a]isoquinolin-4-one, m.p. of the hydrochloride is 119°–121° C.;
(d) starting from 2,3-dimethoxy-α-methylphenethylamine,
8,9-dimethoxy-3,6-dimethyl-2-mesitylimino-2,3,6,7-tetrahydro-4H-pyrimido[6,1-a]isoquinolin-4-one, m.p. of the hydrochloride is 220° C.;
(e) starting from α-methyl-3,4,5-trimethoxyphenethylamine
3,6-dimethyl-2-mesitylimino-2,3,6,7-tetrahydro-9,10,11-trimethoxy-4H-pyrimido[6,1-a]isoquinolin-4-one, m.p. of the hydrochloride is 221° C.;
(f) starting from (α-methyl-3,4-methylenedioxyphenethyl)urea
3,6-dimethyl-2-mesitylimino-9,10-methylenedioxy-2,3,6,7-tetrahydro-4H-pyrimido[6,1-a]isoquinolin-4-one, m.p. of the hydrochloride is 300° C.;
(g) starting from 3-(3,4-dimethoxyphenyl)butylamine via 3-(3,4-dimethoxyphenyl)urea, m.p. of the hydrochloride is 87°–89° C.,
10,11-dimethoxy-3,8-dimethyl-2-mesitylimino-2,3,7,8-tetrahydro-4H,6H-pyrimido[6,1-a]benzazepin-4-one, m.p. of the hydrochloride is 234°–235° C.;
(h) starting from (S)-3,4-dimethoxy-α-methylphenethylamine via 1-[(S)-3,4-dimethoxy-α-methylphenethyl]barbituric acid, m.p. 178°–179° C., $[\alpha]_D$ +93.6° (c=1%, methanol),
1. (S)-6,7-dihydro-9,10-dimethoxy-2-mesitylamino-6-methyl-4H-pyrimido[6,1-a]isoquinolin-4-one, m.p. of the hydrochloride is 196° C., $[\alpha]_D$ +43.3° (c=2%, methanol), and
2. (S)-9,10-dimethoxy-3,6-dimethyl-2-mesitylimino-2,3,6,7-tetrahydro-4H-pyrimido[6,1-a]isoquinolin-4-one,
m.p. of the hydrochloride is 196° C., $[\alpha]_D$ −13° (c=2%, water);
(i) starting from (R)-3,4-dimethoxy-α-methylphenethylamine via 1-[(R)-3,4-dimethoxy-α-methylphenethyl]barbituric acid, m.p. 177°–178° C., $[\alpha]_D$ −92.1° (c=1%, methanol),
1. (R)-6,7-dihydro-9,10-dimethoxy-2-mesitylamino-6-methyl-4H-pyrimido[6,1-a]isoquinolin-4-one, m.p. of the hydrochloride is 196° C., $[\alpha]_D$ −39.6° (c=2%, methanol), and
2. (R)-9,10-dimethoxy-3,6-dimethyl-2-mesitylimino-2,3,6,7-tetrahydro-4H-pyrimido[6,1-a]isoquinolin-4-one, m.p. of the hydrochloride is 195°–196° C., $[\alpha]_D$ +13° (c=2.5%, water);
(j) starting from 1[(S)-3,4-dimethoxy-α-methylphenethyl]-barbituric acid
1. (S)-6,7-dihydro-9,10-dimethoxy-6-methyl-2-(2,6-xylidino)-4H-pyrimido[6,1-a]isoquinolin-4-one, m.p. of the hydrochloride is 182°–183° C., $[\alpha]_D$ +45.6° (c=0.5%, methanol), and
2. (S)-9,10-dimethoxy-3,6-dimethyl-2,3,6,7-tetrahydro-2-(2,6-xylylimino)-4H-pyrimido[6,1-a]isoquinolin-4-one, m.p. of the hydrochloride is 167°–168° C., $[\alpha]_D$ +30.1° (c=2%, methanol);
(k) starting from (S)-3,4-dimethoxy-β-methylphenethylamine via [(S)-3,4-dimethoxy-β-methylphenethyl]urea, m.p. 186°–187° C., $[\alpha]_D$ −41° (c=1%, methanol),
(R)-9,10-dimethoxy-3,7-dimethyl-2-mesitylimino-2,3,6,7-tetrahydro-4H-pyrimido[6,1-a]isoquinolin-4-one,
m.p. of the hydrochloride is 219°–221° C., $[\alpha]_D$ −18.0° (c=2%, methanol);
(l) starting from (R)-3,4-dimethoxy-β-methylphenethylamine via [(R)-3,4-dimethoxy-β-methylphenethyl]urea, m.p. 187°–188° C., $[\alpha]_D$ +45° (c=1%, methanol), (S)-9,10-dimethoxy-3,7-dimethyl-2-mesitylimino-2,3,6,7-tetrahydro-4H-pyrimido[6,1-a]isoquinolin-4-one, m.p. of the hydrochloride is 220°–221° C., $[\alpha]_D +13°$ (c=2%, methanol), (m) starting from (S)-α-ethyl-3,4-dimethoxyphenethylamine via (S)-α-ethyl-3,4-dimethoxyphenethylurea, m.p. 135°–137° C., $[\alpha]_D +11.4$ (c=1%, methanol), 1. (S)-6-ethyl-6,7-dihydro-9,10-dimethoxy-2-mesitylamino-4H-pyrimido[6,1-a]isoquinolin-4-one, m.p. of the hydrochloride is 189°–193° C., $[\alpha]_D +62.5°$ (c=2%, methanol), 2. (S)-6-ethyl-9,10-dimethoxy-2-mesitylimino-3-methyl-2,3,6,7-tetrahydro-4H-pyrimido[6,1-a]isoquinolin-4-one, m.p. of the hydrochloride 166°–170° C., $[\alpha]_D +47.4°$ (c=2%, methanol), 3. (S)-6-ethyl-6,7-dihydro-9,10-dimethoxy-2-(2,6-xylidino)-4H-pyrimido[6,1-a]isoquinolin-4-one, m.p. of the hydrochloride is 171°–175° C., $[\alpha]_D +58.0°$ (c=2%, methanol), and 4. (S)-6-ethyl-9,10-dimethoxy-3-methyl-2,3,6,7-tetrahydro-2-(2,6-xylylimino)-4H-pyrimido[6,1-a]isoquinolin-4-one, m.p. of the hydrochloride is 148°–152° C., $[\alpha]_D +49.4°$ (c=2%, methanol).

EXAMPLE 8

In analogy to Example 3, but using 1-propyl iodide in place of methyl iodide there is prepared 9,10-dimethoxy-2-mesitylimino-7-methyl-3-propyl-2,3,6,7-tetrahydro-4H-pyrimido[6,1-a]isoquinolin-4-one, m.p. of the hydrochloride 152°–154° C.

EXAMPLE A

Tablets of the following composition can be prepared in a manner known to the art:

| | |
|---|---|
| The hydrochloride of a pyrimidone derivative of formula I | 185.0 mg |
| Lactose | 15.0 mg |
| Maize starch | 37.5 mg |
| Water soluble polyvinylpyrrolidone | 10.0 mg |
| Magnesium stearate | 2.5 mg |
| Total weight per tablet | 250.0 mg |

EXAMPLE B

Interlocking gelatine capsules containing the following ingredients can be prepared in a manner known to the art:

| | |
|---|---|
| The hydrochloride of a pyrimidone derivative of formula I | 200.0 mg |
| Water-soluble polyvinylpyrrolidone | 2.0 mg |
| Maize starch | 43.0 mg |
| Talc | 4.5 mg |
| Magnesium stearate | 0.5 mg |
| Total weight per capsule | 250.0 mg |

EXAMPLE C

An injection solution of the following composition can be prepared in a manner known to the art:

| | |
|---|---|
| The hydrochloride of a pyrimidone derivative of formula I | 115.0 mg |
| Glycerinformal | 2.4 ml |
| Water | 4.0 ml |

We claim:

1. A compound of the formula

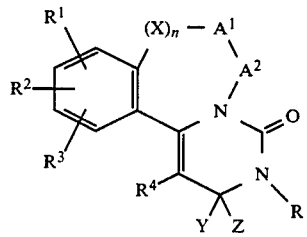

wherein n is the integer 1 or 0; $A^1$ and $A^2$ are independently methylene or mono-lower alkyl or di-lower alkyl methylene; X is methylene, mono-lower alkyl or di-lower alkyl methylene, nitrogen or lower alkyl substituted nitrogen; R is hydrogen or lower-alkyl; Y and Z taken together are the group $=NR^5$, or R and Z taken together form a N—C-bond and Y is a group —N(H)R$^5$; $R^1$, $R^2$ and $R^3$ are hydrogen, lower-alkyl or lower-alkoxy, or $R^1$ and $R^2$ or $R^2$ and $R^3$ taken together are methylenedioxy or ethylenedioxy; $R^4$ is hydrogen or lower-alkyl; $R^5$ is phenyl or phenyl substituted by one or more of $R^6$, $R^7$ and $R^8$ which, independently, are chlorine, fluorine, bromine, lower-alkyl or lower-alkoxy; wherein, each occurrence, lower alkyl is selected from the group consisting of methyl, ethyl, propyl, isopropyl, n-butyl and isobutyl, and lower alkoxy corresponds to the referred to alkyl groups, and provided that at least one of the methylene groups $A^1$ and $A^2$ is mono-lower alkyl or di-lower alkyl methylene when $R^4$ is hydrogen and n is 0, or a physiologically compatible salt thereof.

2. A compound in accordance with claim 1, wherein $A^1$ and $A^2$ are methylene, mono-lower alkyl or di-lower alkyl methylene, X is methylene, mono-lower alkyl or di-lower alkyl methylene, nitrogen or lower alkyl nitrogen, and $R^6$, $R^7$ and $R^8$ are chlorine, bromine, lower-alkyl or lower-alkoxy.

3. A compound in accordance with claim 2, wherein $R^1$ is hydrogen and $R^2$ and $R^3$ are, independently, lower-alkoxy in the para-position to the angular carbon atoms of the phenyl ring.

4. A compound in accordance with claim 3, wherein n is 0 or 1, X is methylene, and one of $A^1$ and $A^2$ is methylene and the other is mono-lower alkylated methylene.

5. A compound in accordance with claim 4, wherein the carbon atom of a mono-lower alkyl methylene group $A^1$ has the R-configuration or the carbon atom of a mono-lower alkyl methylene group $A^2$ has the S-configuration.

6. A compound in accordance with claim 5, wherein R is hydrogen or methyl or R and Z taken together form a N—C-bond.

7. A compound in accordance with claim 6, wherein $R^4$ is hydrogen.

8. A compound in accordance with claim 7, wherein $R^5$ is mesityl or 2,6-xylyl.

9. A compound in accordance with claim 1, (S)-9,10-dimethoxy-3,6-dimethyl-2-mesitylimino-2,3,6,7-tetrahydro-4H-pyrimido[6,1-a]isoquinolin-4-one.

10. A compound in accordance with claim 1, (S)-6-ethyl-6,7-dihydro-9,10-dimethoxy-2-mesitylamino-4H-pyrimido[6,1-a]isoquinolin-4-one.

11. A compound in accordance with claim 1, (S)-6-ethyl-9,10-dimethoxy-2-mesitylimino-3-methyl-2,3,6,7-tetrahydro-4H-pyrimido[6,1-a]isoquinolin-4-one.

12. A compound in accordance with claim 1, (S)-6-ethyl-6,7-dihydro-9,10-dimethoxy-2-(2,6-xylidino)-4H-pyrimido[6,1-a]isoquinolin-4-one and 13. A compound in accordance with claim 1, (S)-6-ethyl-9,10-dimethoxy-3-methyl-2,3,6,7-tetrahydro-2-(2,6-xylylimino)-4H-pyrimido[6,1-a]isoquinolin-4-one.

14. A compound in accordance with claim 1, 6,7-dihydro-9,10-dimethoxy-2-mesitylamino-6-methyl-4H-pyrimido[6,1-a]isoquinolin-4-one.

15. A compound in accordance with claim 1, 9,10-dimethoxy-3,6-dimethyl-2-mesitylimino-2,3,6,7-tetrahydro-4H-pyrimido[6,1-a]isoquinolin-4-one.

16. A compound according to claim 1, 10,11-dimethoxy-2-mesitylimino-3-methyl-2,3,7,8-tetrahydro-4H,6H-pyrimido[6,1-a]benzazepin-4-one.

17. A compound in accordance with claim 1, (S)-6,7-dihydro-9,10-dimethoxy-2-mesitylamino-6-methyl-4H-pyrimido[6,1-a]isoquinolin-4-one.

18. A compound in accordance with claim 1, (S)-9,10-dimethoxy-3,6-dimethyl-2,3,6,7-tetrahydro-2-(2,6-xylylimino)-4H-pyrimido[6,1-a]isoquinolin-4-one.

19. A compound in accordance with claim 1, (S)-6,7-dihydro-9,10-dimethoxy-6-methyl-2-(2,6-xylidino)-4H-pyrimido[6,1-a]isoquinolin-4-one.

20. A compound in accordance with claim 1, (R)-9,10-dimethoxy-3,7-dimethyl-2-mesitylimino-2,3,6,7-tetrahydro-4H-pyrimido[6,1-a]isoquinolin-4-one.

21. A pharmaceutical composition for inhibiting blood platelet aggregation comprising a compound of the formula

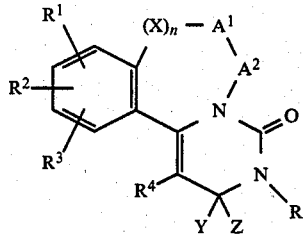

wherein n is the integer 1 or 0; $A^1$ and $A^2$ are independently methylene or mono-lower alkyl or di-lower alkyl methylene; X is methylene, mono-lower alkyl or di-lower alkyl methylene, nitrogen or lower alkyl nitrogen; R is hydrogen or lower-alkyl; and Y and Z taken together are the group $=NR^5$, or R and Z taken together form a N—C bond and Y is a group —N(H)$R^5$; $R^1$, $R^2$ and $R^3$ are hydrogen, lower alkyl or lower alkoxy, or $R^1$ and $R^2$ or $R^2$ and $R^3$ taken together are methylenedioxy or ethylenedioxy; $R^4$ is hydrogen or lower alkyl; $R^5$ is phenyl or phenyl substituted by one or more of $R^6$, $R^7$ and $R^8$ which, independently, are chlorine, fluorine, bromine, lower alkyl or lower alkoxy; wherein, each occurence, lower alkyl is selected from the group consisting of methyl, ethyl, propyl, isopropyl, n-butyl and isobutyl, and lower alkoxy corresponds to the referred to alkyl groups, and provided that at least one of the methylene groups $A^1$ and $A^2$ is mono-lower alkyl or di-lower alkyl methylene when $R^4$ is hydrogen and n is 0, or a physiologically compatible salt thereof, and an inert carrier material.

22. A pharmaceutical composition in accordance with claim 21, wherein $A^1$ and $A^2$ are methylene, mono-lower alkyl or di-lower alkyl methylene, X is methylene, mono-lower alkyl or di-lower alkyl methylene, nitrogen or lower alkyl nitrogen, and $R^6$, $R^7$ and $R^8$ are chlorine, bromine, lower-alkyl or lower-alkoxy).

23. A pharmaceutical composition in accordance with claim 22, wherein $R^1$ is hydrogen and $R^2$ and $R^3$ are, independently, lower-alkoxy in the para-position to the angular carbon atoms of the phenyl ring.

24. A pharmaceutical composition in accordance with claim 23, wherein n is 0 or 1, X is methylene, and one of $A^1$ and $A^2$ is methylene and the other is mono-lower alkylated methylene.

25. A pharmaceutical composition in accordance with claim 24, wherein the carbon atom of a mono-lower alkyl methylene group $A^1$ has the R-configuration or the carbon atom of a mono-lower alkyl methylene group $A^2$ has the S-configuration.

26. A pharmaceutical composition in accordance with claim 25, wherein R is hydrogen or methyl or R and Z taken together form a N—C-bond.

27. A pharmaceutical composition in accordance with claim 26, wherein $R^4$ is hydrogen.

28. A pharmaceutical composition in accordance with claim 27, wherein $R^5$ is mesityl or 2,6-xylyl.

29. A pharmaceutical composition in accordance with claim 21, wherein the compound of formula I is (S)-9,10-dimethoxy-3,6-dimethyl-2-mesitylimino-2,3,6,7-tetrahydro-4H-pyrimido[6,1-a]isoquinolin-4-one.

30. A pharmaceutical composition in accordance with claim 21, wherein the compound of formula I is 9,10-dimethoxy-3,6-dimethyl-2-mesitylimino-2,3,6,7-tetrahydro-4H-pyrimido[6,1-a]isoquinolin-4-one.

31. A method of inhibiting blood platelet aggregation which comprises administration to a host requiring such treatment a compound of the formula

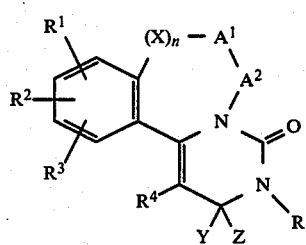

wherein n is the integer 1 or 0; $A^1$ and $A^2$ are independently methylene or mono-lower alkyl or di-lower alkyl methylene; X is methylene, mono-lower alkyl or di-lower alkyl methylene, nitrogen or lower alkyl substituted nitrogen; R is hydrogen or lower-alkyl; and Y and Z taken together are the group=$NR^5$, or R and Z taken together form a N—C bond and Y is a group—N(H)$R^5$; $R^1$ $R^2$ and $R^3$ are hydrogen, lower alkyl or lower alkoxy, or $R^1$ and $R^2$ or $R^2$ and $R^3$ taken together are methylenedioxy or ethylenedioxy; $R^4$ is hydrogen or lower alkyl; $R^5$ is phenyl or phenyl substituted by one or more of $R^6$, $R^7$ and $R^8$ which; independently, are chlorine, fluorine, bromine, lower alkyl or lower alkoxy; wherein, each occurrence, lower alkyl or lower alkoxy; wherein, each occurrence, lower alkyl is selected from the group consisting of methyl, ethyl, propyl, isopropyl, n-butyl and isobutyl, and lower alkoxy corresponds to the referred two alkyl groups, and provided that at least one of the methylene groups $A^1$ and $A^2$ is mono-lower alkyl or di-lower alkyl methylene when $R^4$ is hydrogen and n is 0, or a physiologically compatible salt thereof.

32. A method in accordance with claim 31, wherein $A^1$ and $A^2$ are methylene, mono-lower alkyl or di-lower alkyl methylene, X is methylene, mono-lower alkyl or di-lower alkyl methylene, nitrogen or lower alkyl nitrogen, and $R^6$, $R^7$ and $R^8$ are chlorine, bromine, lower-alkyl or lower-alkoxy.

33. A method in accordance with claim 32, wherein $R^1$ is hydrogen and $R^2$ and $R^3$ are, independently, lower-alkoxy in the para-position to the angular carbon atoms of the phenyl ring.

34. A method in accordance with claim 33, wherein n is 0 or 1, X is methylene, and one of $A^1$ and $A^2$ is methylene and the other is mono-lower alkylated methylene.

35. A method in accordance with claim 34, wherein the carbon atom of a mono-lower alkyl methylene group $A^1$ has the R-configuration or the carbon atom of a mono-lower alkyl methylene group $A^2$ has the S-configuration.

36. A method in accordance with claim 35, wherein R is hydrogen or methyl or R and Z taken together form a N—C-bond.

37. A method in accordance with claim 36, wherein $R^4$ is hydrogen.

38. A method in accordance with claim 37, wherein $R^5$ is mesityl or 2,6-xylyl.

39. A method in accordance with claim 31, (S)-9,10-dimethoxy-3,6-dimethyl-2-mesitylimino-2,3,6,7-tetrahydro-4H-pyrimido[6,1-a]isoquinolin-4—one.

40. A method in accordance with claim 31, wherein the compound of formula I is 9,10-dimethoxy-3,6-dimethyl-2-mesitylimino-2,3,6,7-tetrahydro-4H-pyrimido[6,1-a]isoquinolin-4-one.

41. A method in accordance with claim 26, wherein $A^1$ and $A^2$ are methylene, mono-lower alkyl or di-lower alkyl methylene, X is methylene, mono-lower alkyl or di-lower alkyl methylene, nitrogen or lower alkyl nitrogen, and $R^6$, $R^7$ and $R^8$ are chlorine, bromine, lower-alkyl or lower-alkoxy.

42. A method in accordance with claim 41, wherein $R^1$ is hydrogen and $R^2$ and $R^3$ are, independently, lower-alkoxy in the para-position to the angular carbon atoms of the phenyl ring.

43. A method in accordance with claim 42, wherein n is 0 or 1, X is methylene, and one of $A^1$ and $A^2$ is methylene and the other is mono-lower alkylated methylene.

44. A method in accordance with claim 43, wherein the carbon atom of a mono-lower alkyl methylene group $A^1$ has the R-configuration or the carbon atom of a mono-lower alkyl methylene group $A^2$ has the S-configuration.

45. A method in accordance with claim 44, wherein R is hydrogen or methyl or R and Z taken together form a N—C-bond.

46. A method in accordance with claim 45, wherein $R^4$ is hydrogen.

47. A method in accordance with claim 46, wherein $R^5$ is mesityl or 2,6-xylyl.

48. A method of treating hypertension which comprises administering to a host requiring such treatment a compound of the formula

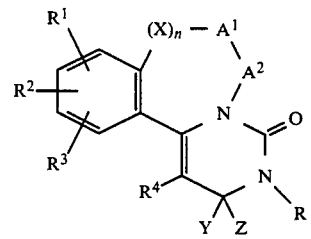

wherein n is the integer 1 or 0; $A^1$ and $A^2$ are independently methylene or mono-lower alkyl or di-lower alkyl methylene; X is methylene, mono-lower alkyl or di-lower alkyl methylene, nitrogen or lower alkyl substituted nitrogen; R is hydrogen or lower-alkyl; and Y and Z taken together are the group =$NR^5$, or R and Z taken together form a N—C bond and Y is a group —N(H)$R^5$; $R^1$, $R^2$ and $R^3$ are hydrogen, lower alkyl or lower alkoxy, or $R^1$ and $R^2$ or $R^2$ and $R^3$ taken together are methylenedioxy or ethylenedioxy; $R^4$ is hydrogen or lower alkyl; $R^5$ is phenyl or phenyl substituted by one or more of $R^6$, $R^7$ and $R^8$ which, independently, are chlorine, fluorine, bromine, lower alkyl or lower alkoxy; wherein, each occurence, lower alkyl is selected from the group consisting of methyl, ethyl, propyl, isopropyl, n-butyl and isobutyl, and lower alkoxy corresponds to the referred to alkyl groups, and provided that at least one of the methylene groups $A^1$ and $A^2$ is mono-lower alkyl or di-lower alkyl methylene when $R^4$ is hydrogen and n is 0, or a physiologically compatible salt thereof.

49. A method in accordance with claim 26, (S)-9,10-dimethoxy-3,6-dimethyl-2-mesitylimino-2,3,6,7-tetrahydro-4H-pyrimido[6,1-a]isoquinolin-4—one.

50. A method in accordance with claim 26, wherein the compound of formula I is 9,10-dimethoxy-3,6-dimethyl-2-mesitylimino-2,3,6,7-tetrahydro-4H-pyrimido 6,1-a isoquinolin-4-one.

* * * * *